United States Patent [19]
Bartnik et al.

[11] Patent Number: 5,399,353
[45] Date of Patent: Mar. 21, 1995

[54] PREPARATIONS FOR COVERING UNDAMAGED AND/OR DAMAGED AREAS OF HUMAN OR ANIMAL SKIN

[75] Inventors: Friedhelm Bartnik, Duesseldorf; Klaus Hachmann, Hilden; Karl Lintner; Wolfgang Pittermann, both of Duesseldorf; Wolfgang Ritter, Haan, all of Germany

[73] Assignee: Henkel Kommanditgesellschaft auf Aktien, Duessledorf, Germany

[21] Appl. No.: 64,952

[22] Filed: Jun. 19, 1987

[30] Foreign Application Priority Data

Jun. 20, 1986 [DE] Germany .................. 36 20 685.7

[51] Int. Cl.$^6$ .................. A61K 9/14; A61K 47/34; A61L 25/00
[52] U.S. Cl. .................. 424/438; 424/78.05; 424/78.06; 424/501; 424/502
[58] Field of Search .................. 560/185; 424/78, 501, 424/502, 78.05, 78.06, 438

[56] References Cited

U.S. PATENT DOCUMENTS

| | | | |
|---|---|---|---|
| 2,668,162 | 2/1954 | Lowe | 260/78.3 |
| 2,676,945 | 4/1954 | Higgins | 260/45.7 |
| 2,703,316 | 3/1955 | Schneider | 260/78.3 |
| 2,721,188 | 10/1955 | Polly et al. | 560/185 |
| 3,297,033 | 1/1967 | Schmitt et al. | 424/78.05 |
| 3,626,948 | 12/1971 | Danbury et al. | 128/335.5 |
| 3,755,558 | 8/1973 | Scribner | 424/47 |
| 4,005,189 | 1/1977 | Reese et al. | 564/554 |
| 4,010,196 | 3/1977 | Tsuk | 560/185 |
| 4,282,250 | 8/1981 | Papogeorgiou | 560/185 |

FOREIGN PATENT DOCUMENTS

| | | |
|---|---|---|
| 100981 | 2/1984 | European Pat. Off. |
| 3000 | 12/1964 | France |
| 2126270 | 10/1972 | France |
| 2418362 | 11/1975 | Germany |
| 3229540 | 9/1984 | Germany |

*Primary Examiner*—Thurman K. Page
*Assistant Examiner*—Peter F. Kulkosky
*Attorney, Agent, or Firm*—Ernest G. Szoke; Wayne C. Jaeschke; Henry E. Millson, Jr.

[57] ABSTRACT

Use of fluid to solid oligomeric esters of lactic acid and/or glycolic acid and dermatologically compatible derivatives thereof as resorbable carriers and/or film formers in preparations for covering undamaged and/or damaged areas of human or animal skin.

19 Claims, No Drawings

PREPARATIONS FOR COVERING UNDAMAGED AND/OR DAMAGED AREAS OF HUMAN OR ANIMAL SKIN

BACKGROUND OF THE INVENTION

1. Field of the Invention

This invention relates to new fluid to solid preparations for covering undamaged and/or damaged skin based on a carrier material compatible with the body.

2. Statement of Related Art

High molecular weight polymers having fiber properties and their use in the field of medicine are known. Well known, for example, are synthetic filament materials, resorbable within the body, based on polyglycolic acid and polylactic acid; see for example U.S. Pat. Nos. 3,297,033; 3,626,948; 2,668,162; 2,676,945; and 2,703,316.

DESCRIPTION OF THE INVENTION

The present invention relates to the use of certain selected oligomeric condensates of lower hydroxycarboxylic acids which constitute this carrier material and which are capable of performing a variety of functions in the application of the preparations of the invention. Not only are the oligomeric products capable of determining the consistency of the preparations, their use and adaptation to the particular application envisaged provides for the production of thinly liquid, ointment- or past-like, wax-like or even sol id preparations. The oligomeric carrier materials can be applied to the skin as non-porous film formers or as powders or dusting powders. All of these various materials are collectively distinguished by their high compatibility with the body and by their high body resorbability. The oligomers used in accordance with the invention are degraded by, and utilized through, metabolic processes of the body. The invention further provides for the control of the time frame during which the oligomeric carrier materials applied remain on the skin, i.e. the period for which these materials remain discernible on the surface of the skin. In particular, it is possible—depending on the resorbability of those parts of the skin which are affected—to prepare, for example, ointment- or paste-like preparations which, applied to the skin as a thin coating, remain on the surface of the skin, i.e. are discernible, for a predetermined period, for example for 10 to 15 hours, before they disappear into the interior of the skin structure. Accordingly, the new oligomeric components are quite generally suitable as carrier materials for the application of active substances to the skin, for example, in the field of cosmetics, in the field of pharmacology, or in the field of disinfection. The oligomeric materials can be used to fix active substances on parts of the Skin for predetermined periods, although they may themselves also be used to perform important functions, for example, in the dressing of wounds or in the cosmetic care of undamaged skin.

It is known that high-polymer esters of selected lower hydroxycarboxylic acids, particularly lactic acid, show high compatibility with the body and are used in surgery, for example as body-compatible and body-resorbable thread. These high-polymer lactides are degraded over a period of weeks or months and, finally, are washed out of the body through the metabolism. The implantation of solid preforms of high molecular weight polylactic acid in the human and/or animal body has also been intensively researched and the degradation of these implantates in the body, which generally lasts for months, takes place without long-lasting disturbance of the organism.

The present invention is based on the utilization of the pharmacological acceptability of selected polyesters and the capacity of the living organism for resorption through metabolic processes of the body involving compounds of this class in a molecular weight range of the above polyesters which is far below that of materials hitherto used for this purpose. More particularly, the invention seeks to use body-resorbable products having a consistency range extending from thinly liquid via paste-like, wax-like, through to solids and to utilize these body-compatible and body-resorbable oligoesters in various ways as a carrier material, although this carrier material may also have a function of its own to perform in terms of its application.

In a first embodiment, therefore, the present invention relates to the use of liquid to solid oligomeric esters of lactic acid and/or glycolic acid and/or dermatologically compatible derivatives thereof as a resorbable carrier and/or film former in preparations for covering undamaged and/or damaged areas of human or animal skin. The oligomers according to the invention are distinguished by an average degree of oligomerization of the hydroxycarboxylic acids selected of up to about 100 and preferably of up to about 50, an average degree of oligomerization of only up to about 35 units of the hydroxycarboxylic acid selected being sufficient to ensure a satisfactory consistency range from thinly liquid to solid, taking into account the further possibilities of combination of the oligomers with other body-compatible components discussed hereinafter. As the following Examples show, degrees of oligomerization in characteristic oligomer derivatives of up to only 25 and, more especially, of the order of 2 or 3 to 25 can provide, on the one hand, for thinly liquid oils and ointment-, paste- or cream-like compositions and, on the other hand, for solid, hard materials which can be reduced to powders.

Glycolic acid and lactic acid are lower hydroxycarboxylic acids which occur in the healthy metabolism of the living organism and which may be digested and secreted by the body. The lactic acid can be used in the form of its racemate or in the form of its optical antipodes (more especially in the l-form occuring in natural metabolism) or in the form of mixtures of the optical antipodes.

Due to the monomer structure, oligomers and polymers of hydroxycarboxylic acids, in the same way as the monomers, have a residual content of free hydroxyl groups and free carboxyl groups. The presence of free carboxyl groups, in particular, can be of considerable importance to the invention. Where the preparations of the invention are applied to wounds and particularly to fresh wounds which are still bleeding, the presence of free carboxyl groups leads to coagulation of the blood and hence to desirable healing of the wound. On the other hand, the presence of free carboxyl groups can also displace the pH-value of the preparations into the dermatologically often desirable mildly acidic range so that, even when the new preparations are used on undamaged skin, entirely desirable effects can be obtained by means of the free carboxyl groups. On the other hand, however, the presence of carboxyl groups, particularly free carboxyl groups, is consciously avoided for certain other applications.

Both for this particular case and, quite generally, for the derivatization of the oligomers of the invention, it is possible to use the two ester-forming groups of the monomers or the oligomers, i.e. the hydroxyl group on the one hand and the carboxyl group on the other hand. Both reactive sites are suitable for the formation of simple chemical modifications, particular significance again being attributed to those derivatives which do not impair the desired body compatibility and/or resorbability of the materials through the metabolism. On the contrary, significant influence may be exerted on the above-mentioned possibility of controlling the permanence of the material on the surface of the skin through the use of other body-compatible reactants. The oligomers may be derivatized, in particular by esterification, with reactants containing hydroxyl groups or carboxyl groups which satisfy the above-mentioned requirements, particularly compatibility with the body.

Accordingly, the oligomeric lactic acid and/or glycolic acid esters can be attached to monofunctional and/or polyfunctional alcohols and/or to monobasic and/or polybasic carboxylic acids. In preferred embodiments, esters suitable for attachment to alcohols are corresponding esters with alcohols containing up to 4 and more especially up to 3 hydroxyl groups, among which monofunctional alcohols are particularly important, although on the other hand difunctional and in particular trifunctional alcohols can also be of importance. In the last-mentioned case, it is especially glycerides which lead to extremely diverse and very interesting products and product properties when used to esterify the glycolic acid and/or lactic acid oligomers according to the invention. Where carboxylic acids are used for esterification, physiologically compatible carboxylic acids, particularly monocarboxylic acids, can be employed, although on the other hand polybasic carboxylic acids, for example di- or tricarboxylic acids, also lead to interesting and physiologically acceptable oligomer derivatives for various applications.

The oligomeric hydroxycarboxylic acids or derivatives thereof are prepared by known methods. Oligomers of glycolic acid and/or lactic acid, where no other reactants are used, can be prepared, for example, by known condensation of the monomeric and/or dimeric starting materials, for example the lactide consisting of two lactic acid residues. In this instance, the polycondensation reaction is normally carried out by heating the starting material to a temperature above its melting point in the presence of catalysts, for example in the presence of polyvalent metal oxides or compounds thereof, under anhydrous conditions in an inert gas atmosphere. Suitable catalysts are, for example, tin oxide or tin salts, such as tin carbonate, basic tin carbonate, tin diethyl, aluminum, titanium, magnesium, barium and/or lead compounds. The type and quantity of catalyst used determine the process temperature and reaction time. It is advisable to stir the reaction mixture during the polymerization to ensure that a homogeneous reaction or reaction mixture is obtained. The reaction can be carried out in several steps by working under multistep temperature and/or multistep pressure conditions, normal pressure being applied, for example, at the beginning of the reaction and reduced pressures during the course of the reaction. The polycondensation reaction is continued to the desired average degree of oligomerization. The reaction product may then be freed in the usual way from the catalysts used, where the presence of these catalysts could be regarded as objectionable in the application of the oligomeric products to the skin.

In important embodiments of the invention, reactive derivatives of the free hydroxycarboxylic acids, particularly esters thereof with lower alcohols, are used in addition to and/or instead of the free hydroxycarboxylic acids. Thus, both glycolic acid and lactic acid may be used for example in the form of their esters with monoalcohols containing from 1 to 3 C-atoms, particularly ethyl esters. On the other hand, however, where monofunctional alcohols are used as co-reactants, linear, relatively long-chain monoalcohols, e.g. the so-called fatty alcohols, i.e. alcohols containing from 8 to 22 and more especially from 10 to 18 carbon atoms can be employed. They may be of natural and/or synthetic origin. Insofar as the compatibility of these co-reactants with the body is concerned, general knowledge about the compatibility of these compounds applies here. They are generally absorbed without difficulty into the metabolism of the body. Hardened, relatively long-chain alcohols, for example of the tallow alcohol type, are capable of establishing or rather initiating certain property parameters in regard to consistency and/or in regard to the permanence of the oligomeric reaction product on the skin. Relatively long-chain alcohols, in particular, can be saturated or unsaturated, and can optionally contain pharmacologically acceptable functional groups or substituents.

Monofunctional alcohols of the type discussed above can be used as starter components and can be reacted with the hydroxycarboxylic acids as such or with reactive derivatives thereof, for example esters with lower alcohols. Where polyfunctional alcohols are used, lower polyfunctional alcohols are particularly suitable as co-reactants. Ethylene glycol, glycerol and trimethylol propane are examples of such lower polyfunctional alcohols. Of particular importance are ethylene glycol and especially glycerol. Glycerol is a particularly suitable co-reactant, which opens up the possibility of making available oligomer-substituted mono-, di- and/or triglycerides having a variety of different properties with respect to consistency and permanence on the skin. The general rules discussed hereinafter with reference to glycerides also apply to other polyfunctional alcohols.

Natural or synthetic fats are generally triglycerides from the reaction of glycerol and monocarboxylic acids. Modified fats can be obtained by partial cleavage of triglycerides or by partial esterfication of glycerol with a sub-equivalent quantity of monocarboxylic acids, i.e. to form monoglycerides or diglycerides. Through the incorporation of oligomeric units of glycolic acid and/or lactic acid in glyceride linkage and in particular through the incorporation of the oligomeric structural elements in fats or partial fats of natural and/or synthetic origin, it is possible to produce carrier materials suitable for the purposes of the invention in a range of almost unlimited extent from oily substances to hard fats. The range extending from still spreadable, viscous ointment-like substances to contact-dry, for example more wax-like products can be of particular interest. In this case, the starting point may be natural fats and/or oils which are converted into the oligomer-modified carrier materials of the invention simply by co-condensation with lactic acid and/or glycolic acid. Accordingly, the products obtained in this way are complex mixed esters which, in addition to the polyfunctional alcohol and the oligomeric hydroxycarboxylic acid structural units, also contain the original monocarboxylic acids of the triglyceride used. Through the character of the carboxylic acids of relatively high carbon count, such as occur for example in natural oils, fats and/or waxes, it is again possible to influence the overall quality of the condensate containing oligomer units, thus making it possible in the broadest sense to determine consistency in advance by predetermining the structure of the complex polyester product. At the same time, however, it is also possible to adapt the period for which the composition remains on the skin, i.e. its permanence, to the particular application envisaged. A normal fatty cream of the type used, for example, in cosmetics or in dermatology has been absorbed to such an extent by the skin after a comparatively short time, for example 15 to 30 minutes, that a continuous fatty film is no longer externally discernible. This may be desirable. However, there are numerous applications where, conversely, it would be desirable to ensure a comparatively long permanence of the fatty film, but at the same time to be certain that, after a predeterminable time of, for example, 10 to 20 hours, the substrate has been taken up by the skin. A simple example of this is the fixing of active substances to the skin; skin-care, regenerating and/or disinfecting agents being of primary importance in the field of cosmetics, and disinfecting and/or wound-healing agents being of equal importance in the medical field, whereas the application of pharmacological agents effective over prolonged periods may be desirable in pharmacological applications. The invention opens up new possibilities here of applying active agents of any kind to undamaged and/or damaged human or animal skin.

In addition to the pasty, ointment-like compositions discussed above, another particularly interesting application is the dressing of wounds in the field of self-medication and also in general practice and in hospitals, where considerable importance is attributed to vulnerary powders. Although there are in fact numerous sol ids powders, they are often limited in their application. This is always the case when the powder-forming solid material is not resorbable by the body, so that powder articles interfere with the healing process or have to be eliminated by the body in the course of the healing process. By contrast, vulnerary powders using the carrier materials of the invention ideally satisfy the requirement of instantly closing the wound as required while, at the same time, allowing it to breathe, absorbing the exudate and accelaratiang the granulation process. That variant of the invention, in which free carboxyl groups are used in the oligomeric carrier, can be particularly effective in this regard. When a powder of this type is applied to an open wound, a kind of artificial scab is formed with the aid of the wound fluid, which does not interfere with the natural granulation and wound-healing process.

The observations made with reference to the mono- and/or polyfunctional alcohols also apply to the use of carboxylic acids as co-reactants. This is clear from the structure of the hydroxycarboxylic acids forming the oligomers and their ability to form ester bonds both through the carboxyl group and through their hydroxyl group.

Accordingly, suitable monocarboxylic acids are those containing, for example, up to about 22 C-atoms and preferably up to about 18 C-atoms, preferably natural and/or synthetic saturated or olefinically unsaturated carboxylic acids containing from about 10 to about 18 C-atoms. However, shorter chain monocarboxylic acids are also suitable in the absence of dermatological and/or other pharmacological objections, e.g. those having from 2-9 C-atoms, preferably 2-6 C-atoms.

Corresponding considerations apply to the use of polycarboxylic acids, particularly di- and/or tricarboxylic acids. In their case, too, preferred are the corresponding shorter chain carboxylic acids containing in all up to 10 and preferably up to 6 C-atoms, e.g. from 2 to 6 C-atoms.

By using polyfunctional and monofunctional reactants together on the alcohol and/or carboxylic acid side, it is possible to produce comparatively complex condensation products, although according to the invention they are always distinguished by the presence of oligomeric lactic acid and/or glycolic acid units, crucial importance being attributed to these oligomer units in co-operation with the other selected co-reactants.

According to the invention, use may be made of another principle for adjusting, In particular, the consistency of solids, namely: the free carboxyl groups which are present in the oligomeric reaction products can be converted into their salts. Known, pharmacologically acceptable bases can be used for this purpose.

The formulation of the active-substance mixtures ultimately used comprises the broad field of dressing healthy, diseased, and/or damaged skin and the treatment of the organism with medicaments through the skin both in human beings and in animals, particularly In mammals. The possibilities for mixing and preparing active-substance mixtures using the oligomer components according to the invention are equally numerous. Insofar as the field of skin care covered by the invention is concerned, it is of particular advantage that the oligomeric reaction products are converted into neutral substances by masking of all functional groups, so that they can be mixed without difficulty with any active substances or other auxiliary components. On the other hand, it is of particular advantage that limited quantities of free carboxyl groups are formed in situ at the latest during the hydrolytic attack on the oligomeric structure, these free carboxyl groups being capable of reducing the pH-value of the skin surface to the desirable mildly acidic range. As already mentioned, it is also possible to use free carboxyl groups from the outset and hence to initiate specific effects, particularly blood-staunching coagulation.

The compatibility of the oligomers of the invention with standard skin-care components or auxiliaries used in comparable preparations is good. Thus, standard solvents and/or emulsifiers can be used for the production of liquid preparations which are subsequently used, for example, in the form of sprays or liquid lotions. Emulsified active-substance concentrates using the film-forming carrier substances of the invention can be diluted with water for application and subsequently applied. Mixing with standard, oily or ointment- or paste-like skin treatment or skin-protecting preparations is readily possible where the present oligomer substrates are used. It is possible, for example, to vary and more especially to extend the permanence of the mixture used on the skin through the use of the oligomer substrates of the invention. Powder-form preparations of oligomer components of the invention can be mixed with other powder-form components used in skin and wound care in order to enhance certain desired effects, for example, to enhance the absorbing effect of the powder applied on secretions, or utilization of the film-forming property to prevent the penetration of pathogenic microorganisms.

From the wide range of applications of the active-substance mixtures of the invention, the following are given purely by way of example: cosmetics with their broad range of skin-care, regenerating or purely ornamental additives; the field of protective substances in preventive medicine, for example in child care, more especially ointments and/or powders, protective ointments against strong UV-irradiation with permanence on the skin extended in accordance with the invention; the broad field of disinfection of undamaged and/or damaged skin, including the mucous membrane, and finally the field of application of pharmacological preparations through the skin with delayed release of the active substances.

According to the invention, it is possible to satisfy very specific requirements which could not be comparably satisfied with hitherto known preparations. The field of cow udder disinfection is mentioned as an example in this regard. The preventive disinfection of cows' udders requires the fixing of disinfectants on the teats and, more especially, in the region of the milk duct for a period of from about 10 to 12 hours. However, where milking is carried out twice daily, no significant residue of the disinfectant and/or of the auxiliaries and carriers used together with the disinfectant should be present at the time of milking. Hitherto, lasting disinfection of the udder region has either only been possible for a short period, for example 2 to 3 hours, or it has been necessary to use auxiliaries and carriers of the type whose permanence far exceeds the desired time of 10 to 12 hours. Thus, attempts have been made to provide relatively long-lasting protection against the penetration of pathogenic microorganisms through the formation of films by means of polymer compounds. However, this means that, at the next milking, the teat region has to be carefully cleaned, otherwise residues of the polymer compound and hence disinfectants enter the milk and contaminate According to the invention, It is possible for the first time, by regulating the permanence of the carrier material to the desired time of 10 to 12 hours, to apply standard disinfectants simply and safely in the carriers of the invention; a protective film being formed which, at the time of the next milking, but not until then, has been absorbed by the udder tissue and, hence, does not interfere with the next milking.

The preparations according to the invention for covering undamaged and/or damaged skin can contain the carrier material containing oligomer segments In quantities of from about 5 to almost 100%, since application in the absence of other auxiliaries, i.e. application of the pure oligomer, is also advantageous. The quantity of the particular active substances added will depend upon the general requirements of the field of application. Strong disinfectants, for example germicidal, antibiotic and/or sulfonamide-containing agents, can be very effective in very low concentrations of from 0.1 to 1% by weight, while other disinfectants, for example of the oxidizing or non-oxidizing type, such as hydrogen peroxide, urea perhydrate, benzoyl peroxide, glucose oxidase, lactic acid, PVP-iodine, chlorhexidine, quaternary ammonium compounds, undecylenic acid amides, lysozyme, oxoferine and the like, can be used in larger quantities. Examples of skin-care and/or healing agents are vitamin E, vitamin C, allantoin, propolis, pantothenyl alcohol, Melissa officinalis, oxoferine and the like. In powder-form preparations, saccharin, d-lactose and also inorganic powder components, such as Aerosil, zinc oxide and the like, can be used as additional secretion-absorbing components. Suitable solvents for the production of liquid preparations are, in particular, lower alcohols, for example ethanol, isopropanol, n-propanol, propylene glycol, glycerol and the like. The invention will be illustrated but not limited by the following examples.

EXAMPLES

The following Examples illustrate the production and physical characteristics of a number of oligomeric hydroxycarboxylic acid derivatives. The compounds involved are divided into the following 5 classes:

1. Reaction products of diols and triols with hydroxycarboxylic acid derivatives
   a) ethylene glycol/glycerol × glycolic acid
   b) ethylene glycol/glycerol × lactic acid
   c) ethylene glycol/glycerol × lactic acid ethyl ester
   d) ethylene glycol/glycerol × glycolic acid/lactic acid ethyl ester
   e) ethylene glycol/glycerol × lactide 2. Reaction products of monoalcohols with hydroxycarboxylic acid derivatives
   a) monoalcohol × glycolic acid
   b) monoalcohol × lactic acid
   c) monoalcohol × lactic acid ethyl ester
   d) monoalcohol × lactide 3. Reaction products of dicarboxylic acids with hydroxycarboxylic acids
   a) adipic acid × glycolic acid 4. Reaction products of glycerol with hydroxycarboxylic acids and fatty acids
   a) glycerol × glycolic acid × fatty acid
   b) glycerol × lactic acid × fatty acid
   c) glycerol × glycolic acid/lactic acid × fatty acid 5. Reaction products of fatty acid mono- and diglycerides with lactide
   a) glycerol monoester × lactide
   b) glycerol diester × lactide

1. Reaction Products of Diols and Triols with Hydroxycarboxylic Acid Derivatives a) Ethylene glycol/glycerol × glycolic acid
Procedure:

Glycolic acid and ethylene glycol or glycerol were initially introduced into a three-necked flask equipped with a stirrer and distillation bridge. The contents of the flask were rapidly heated under nitrogen to 150° C. and then from 150° to 200° C. over a period of 6 hours, during which most of the water of reaction (indicating the conversion of the ester condensation) was eliminated. The reaction mixture was left to cool to around 150° C., carefully evacuated to 10 Torr and the reaction completed at 200° C./10 Torr. After 30 minutes, the product was decanted at around 150° C. The composition of the mixtures and the oligomer properties are shown in the Table 1.

TABLE 1

Reaction products of ethylene glycol/glycerol and glycolic acid

| Example no. | Diol, triol | Molar ratio glycolic acid: diol or triol | Molecular weight (theor.) | Viscosity | Color |
|---|---|---|---|---|---|
| 1 | ethylene glycol | 3:1 | 236 | liquid, viscous | colorless |
| 2 | ethylene glycol | 4:1 | 294 | viscous | yellowish |
| 3 | ethylene glycol | 6:1 | 410 | paste-like | white |
| 4 | glycerol | 3:1 | 266 | highly viscous | yellowish |
| 5 | glycerol | 6:1 | 440 | highly viscous, paste-like | yellowish | b) Ethylene glycol/glycerol × lactic acid
Procedure:

In a laboratory stirring apparatus equipped with a distillation bridge, the quantities of lactic acid and ethylene glycol indicated in Table 2 were slowly heated under nitrogen to 210°-220° C. (2-4 hours). The water of reaction and, at the same time, the water from the lactic acid (90% in $H_2O$) distilled over.

In order to complete the reaction, the reaction mixture was then cooled to around 150° C. and a water jet vacuum was applied for 30 minutes at that temperature. For purification, the product was cooled to around 90° C., fuller's earth was added (Tonsil LFF 80, 5% based on lactic acid, manufactured by Südchemie, München, Germany), the whole was stirred for 30 minutes and then filtered under suction through a superheated-steam vacuum filter with filtering aid. The product was decanted without cooling. Fascat 2001 (0.5%, based on lactic acid, an Sn catalyst manufactured by Neynaber Chemie, Loxstedt, Germany) was used as catalyst.

The diol or triol and lactic acid ethyl ester were initially introduced into an apparatus of the type described in 1. a), evacuated four times, purged with nitrogen on each occasion and then heated in a gentle stream of nitrogen to a bath temperature of 160° C. 340 mg of a 30% by weight solution of $NaOCH_3$ in methanol were added per mole lactic acid ethyl ester at a sump temperature of approximately 60° C. The reaction mixture was then slowly further heated until ethanol distilled over for the first time at a bath temperature of approximately 190° C. (sump temperature approx. 150° C.). The bath temperature was gradually increased to 230° C. When no more ethanol distilled over, the reaction mixture was left to cool and a water jet vacuum subsequently applied. The reaction mixture was then slowly heated again to 150° C. and the remaining ethanol thus distilled off in the water jet vacuum. The product was decanted without cooling.

d) Ethylene glycol or glycerol × glycolic acid and lactic acid ethyl ester

TABLE 2

Reaction products of ethylene glycol/glycerol with lactic acid

| Example no. | Diol-triol | Molar ratio lactic acid: diol | Molecular weight (theor.) | OH number measured | Viscosity | Color |
|---|---|---|---|---|---|---|
| 6 | ethylene glycol | 3 | 278 | 343 | slightly viscous | pale yellow, clear |
| 7 | ethylene glycol | 24 | 1793 | 80 | highly viscous | yellow, clear | c) Ethylene glycol/glycerol × lactic acid ethyl ester
Procedure:

Procedure:
See 1. a), 1. c).

TABLE 3

Reaction product of ethylene glycol/glycerol with lactic acid ethyl ester

| Example no. | Diol or triol | Molar ratio lactic acid ethyl ester: diol or triol | Molecular weight (theor.) | Viscosity | Color |
|---|---|---|---|---|---|
| 8 | ethylene glycol | 2:1 | 206 | thinly liquid | yellow |
| 9 | ethylene glycol | 4:1 | 351 | slightly viscous | dark |
| 10 | ethylene glycol | 6:1 | 495 | viscous | dark |
| 11 | ethylene glycol | 10:1 | 787 | viscous | dark |
| 12 | glycerol | 6:1 | 525 | viscous | dark |
| 13 | glycerol | 12:1 | 957 | highly viscous | dark |

TABLE 4

Reaction products of ethylene glycol or glycerol with glycolic acid and, at the same time, lactic acid ethyl ester

| Example no. | Adducts a | b | c | Molar ratio a:b:c | Molecular weight (theor.) | Viscosity | Color |
|---|---|---|---|---|---|---|---|
| 14 | glycolic acid | lactic acid ethyl ester | ethylene glycol | 5:1:1 | 424 | viscous | yellowish |
| 15 | glycolic acid | lactic acid ethyl ester | ethylene glycol | 4:2:1 | 438 | highly viscous | pale yellowish |
| 16 | glycolic acid | lactic acid ethyl ester | ethylene glycol | 10:2:1 | 786 | paste-like | yellowish |

TABLE 4-continued

Reaction products of ethylene glycol or glycerol with glycolic acid and, at the same time, lactic acid ethyl ester

| Example no. | Adducts a | b | c | Molar ratio a:b:c | Molecular weight (theor.) | Viscosity | Color |
|---|---|---|---|---|---|---|---|
| 17 | glycolic acid | lactic acid ethyl ester | ethylene glycol | 8:4:1 | 815 | paste-like partly crystalline | yellowish |
| 18 | glycolic acid | lactic acid ethyl ester | glycerol | 5:1:1 | 454 | highly viscous | yellow | e) Ethylene glycol/glycerol×lactide
Procedure:

In a standard laboratory apparatus, lactide and ethylene glycol or glycerol were heated with stirring for one hour under nitrogen to a temperature of 195° C. The mixture was then left to react for 3 hours at 195° C. and decanted without cooling. An Sn-II-chloride solution in ether was present as catalyst (7 ml of a solution of 2.5 g SnCl$_2$ in 1000 ml ether in the reaction of 3 moles lactidé with 1 mole ethylene glycol).

minutes. Water of reaction distilled off beyond a bath temperature of 190° C. (sump temperature 155° C.). At the end of the reaction, the sump temperature had reached 200° C. The reaction mixture was then left to cool to 150° C. and the remaining water was distilled off in a water jet vacuum. The product was decanted under nitrogen without cooling. Typical overall reaction times were from 3 to 4 hours.

TABLE 6

| | Reaction products of tallow alcohol and glycolic acid | | | | |
|---|---|---|---|---|---|
| | Adducts/Mole | | Product properties | | |
| Example no. | tallow alcohol | glycolic acid | consistency, color | hydroxyl number theor. | found | acid number |
|---|---|---|---|---|---|---|
| 26 | 1 | 1 | solid, pale beige | 176.4 | 181.2 | 4.8 |
| 27 | 1 | 2 | solid, pale beige | 143.2 | 148.1 | 17.2 |
| 28 | 1 | 4 | solid, pale beige | 114.1 | 101.2 | 24 |
| 29 | 1 | 8 | solid, white | — | — | 37 | b) Monoalcohol×lactic acid
Procedure:

TABLE 5

Reaction products of ethylene glycol or glycerol with lactide

| Example no. | Diol or triol | Molar ratio lactide: diol or triol | Molecular weight (theor.) | OH number (measured) | Brookfield viscosity | Spindle | | Rotational speed (min$^{-1}$) | Water solubility | Fluidity |
|---|---|---|---|---|---|---|---|---|---|---|
| 19 | ethylene glycol | 1.5 | 278 | 386 | 0.88 | mPa.s | 5 | 50 | + | + |
| 20 | ethylene glycol | 3.0 | 494 | 191 | 50 | mPa.s | 7 | 10 | — | + |
| 21 | ethylene glycol | 6.0 | 926 | 89.3 | 8000 | mPa.s | 7 | 0.5 | — | — |
| 22 | ethylene glycol | 12.0 | 1790 | 45.6 | >8000 | mPa.s | 7 | 0.5 | — | — |
| 23 | glycerol | 1.5 | 308 | 487 | 16.1 | mPa.s | 5 | 10 | + | + |
| 24 | glycerol | 3.0 | 524 | 275 | 720 | mPa.s | 7 | 1 | — | — |
| 25 | glycerol | 6.0 | 956 | 151 | 8000 | mPa.s | 7 | 0.5 | — | — |

+ = fluid
− = non-fluid

2. Reaction Products of Monofunctional Alcohols with Hydroxycarboxylic Acid Derivatives a) Monoalcohol×glycolic acid
Procedure:

All the adducts were initially introduced into a 500-ml three-necked flask equipped with a KPG stirrer with a PTFE blade, thermometer, nitrogen inlet and distillation bridge with condenser, receiving flask and bubble counter. The reaction vessel was evacuated four times, purged with nitrogen on each occasion and then heated in a gentle stream of nitrogen to a bath temperature of 180° C. The reaction mixture melted at a sump temperature of approximately 80° C. The bath temperature was then increased to 230° C. in stages of 10° C. every 15

In a laboratory stirring apparatus with a distillation bridge, the quantities of lactic acid and tallow alcohol indicated in Table 7 were slowly heated under nitrogen to 210°-220° C. (6-8 hours). The water of reaction and the water from the lactic acid (90% in H$_2$O) distilled over. To complete the reaction, the reaction mixture was subsequently cooled to around 150° C. and a water jet vacuum applied for 30 minutes at that temperature. For purification, the product was cooled to around 90° C., fuller's earth was added (Tonsil LFF 80, 5% based on lactic acid), the whole stirred for 30 minutes and then filtered under suction through a superheated-steam vacuum filter with filtering aid. The product was decanted without cooling. Frascat 2001 (0.5%, based on lactic acid) was used as catalyst.

TABLE 7

| | Reaction products of tallow alcohol and lactic acid | | | | | | |
|---|---|---|---|---|---|---|---|
| | Adducts/mole | | | | | | |
| Example no. | tallow alcohol | lactic acid | Water of reaction | Hydroxyl number theor. | found | Acid number | Consistency and color |
|---|---|---|---|---|---|---|---|
| 30 | 1 | 1 | 100% | 167 | 169.1 | 1.9 | wax-like, soft; white |

TABLE 7-continued

Reaction products of tallow alcohol and lactic acid

| Example no. | Adducts/mole tallow alcohol | lactic acid | Water of reaction | Hydroxyl number theor. | found | Acid number | Consistency and color |
|---|---|---|---|---|---|---|---|
| 31 | 1 | 2 | 100% | 137.5 | 142.5 | 11.7 | wax-like, soft; white |
| 32 | 1 | 4 | 100% | 101.6 | 116.7 | 28.7 | wax-like, soft; white | c) Monoalcohol×lactic acid ethyl ester
Procedure:

The tallow fatty alcohol and lactic acid ethyl ester were initially introduced into an apparatus of the type described in 2 a), evacuated four times, purged with nitrogen on each occasion and then heated in a gentle stream of nitrogen to a bath temperature of 160° C. When the reaction mixture had melted at a sump temperature of around 60° C., 340 mg of a 30% by weight solution of $NaOCH_3$ in methanol were added per mole lactic acid ethyl ester. The reaction mixture was then slowly further heated until ethanol distilled over for the first time at a bath temperature of around 190° C. (sump temperature approx. 150° C.). The bath temperature was gradually increased to 230° C. When ethanol stopped distilling over, the reaction mixture was left to cool to just above the crystallization temperature and was then evacuated by application of a water jet vacuum. The mixture was then slowly heated again to 150° C. and the remaining ethanol thus distilled in the water jet vacuum. The product was decanted without cooling.

TABLE 7a

Reaction products of tallow alcohol and lactic acid ethyl ester

| Example no. | Adducts/mole tallow alcohol | lactic acid ethyl ester | Consistency/color | Product properties yield ethanol dist. off % | hydroxyl number theor. | found | acid number |
|---|---|---|---|---|---|---|---|
| 33 | 1 | 1 | solid, pale yellow | 98 | 168.9 | 176.9 | 0.3 |
| 34 | 1 | 2 | solid, pale yellow | 100 | 138.9 | 151.3 | 0.4 |
| 35 | 1 | 4 | liquid with crystal sludge, greasy brown | 100 | 102.3 | 145.6 | 1.5 |
| 36 | 1 | 8 | thinly liquid, black | 96 | 67.1 | — | — | d) Monoalcohol×lactide
Procedure:

Alcohol, lactide and—per mole lactide—2.3 ml of a solution of 2.5 mg $SnCl_2$ per ml ether were combined in an apparatus of the type described in 1. a). The apparatus was evacuated and purged with nitrogen four times. The components were heated for 1 hour to 190°–195° C. in a gentle stream of nitrogen. The reaction mixture was then left to react for 3 to 3.5 hours at 190° to 195° C. The product was decanted without cooling.

TABLE 8

Reaction products of monoalcohols and lactide

| Example no. | Adducts alcohol (1 mole) | lactide (mole) | Product properties consistency, color | hydroxyl number theor. | found |
|---|---|---|---|---|---|
| 37 | decanol | 0.5 | liquid, colorless | 244 | 239 |
| 38 | decanol | 2 | liquid, colorless | 126 | 117 |
| 39 | tallow fatty alcohol | 0.5 | wax-like, white | 167 | 169 |
| 40 | tallow fatty alcohol | 1 | wax-like, white | 137 | 143 |
| 41 | tallow fatty | 2 | wax-like, white | 112 | 107 |
| 42 | alcohol tallow fatty alcohol | 4 | wax-like, white | 67 | 73 |
| 43 | behenyl alcohol | 0.5 | solid, colorless, cloudy | 142 | 132 |
| 44 | behenyl alcohol | 2 | solid, colorless, cloudy | 92 | 88 |

3. Reaction Products of Dicarboxylic Acids with Hydroxycarboxylic Acids

Procedure:

Dicarboxylic acid and hydroxycarboxylic acid are introduced into a three-necked flask equipped with a stirrer and distillation bridge. The contents of the flask are then rapidly heated under nitrogen to 150° C. and then from 150° to 200° C. over a period of 6 hours, during which most of the water of reaction (indicating the conversion of the ester condensation) is eliminated. The mixture is left to cool to around 150° C., carefully evacuated to 10 Torr and the reaction subsequently completed at 200° C./10 Torr. The product is decanted under nitrogen without cooling. The composition of the mixtures and the oligomer properties are shown in Table 9.

TABLE 9

Reaction products of adipic acid and glycolic acid

| Example no. | Adducts glycolic acid mole | adipic acid mole | Yield water of reaction % | Consistency |
|---|---|---|---|---|
| 45 | 1 | 1 | 99 | wax-like, solid |
| 46 | 1.5 | 1 | 90 | paste-like, soft |
| 47 | 2 | 1 | 99 | paste-like, soft |
| 48 | 2.5 | 1 | 95 | wax-like, soft |
| 49 | 3 | 1 | 98 | wax-like, soft |
| 50 | 4 | 1 | 96 | wax-like, soft |
| 51 | 5 | 1 | 93 | wax-like, hard |
| 52 | 5.5 | 1 | 91 | wax-like, hard |
| 53 | 6 | 1 | 92 | wax-like, hard |

TABLE 9-continued

| | Reaction products of adipic acid and glycolic acid | | | |
|---|---|---|---|---|
| | Adducts | | | |
| Example no. | glycolic acid mole | adipic acid mole | Yield water of reaction % | Consistency |
| 54 | 20 | 1 | 92 | wax-like, very hard |

4. Reaction Products of Glycerol with Hydroxycarboxylic Acids and Fatty Acids Procedure:

The quantities of adducts indicated in Tables 10 to 12 were heated under nitrogen for 5 hours to 210°–220° C. in a laboratory stirring apparatus equipped with a distillation bridge. Fascat 2001 (0.5%, based on lactic acid) was used as catalyst. Both the water of reaction and the water from the lactic acid used (90% in $H_2O$) distilled over.

To complete the reaction, the reaction mixture was subsequently cooled to around 150° C. and a water jet vacuum applied for 30 minutes at that temperature. For working up, the product was cooled to around 120° C., fuller's earth was added (Tonsil LFF 80, 5% based on lactic acid), the mixture was stirred for 30 minutes and then filtered under suction through a superheated-steam vacuum filter with filtering aid. The product was decanted without cooling.

Details of the laboratory mixtures and product properties are shown in Tables 10 to 12.

TABLE 10

| | Reaction products of glycerol, glycolic acid, fatty acid | | | | | | |
|---|---|---|---|---|---|---|---|
| Example no. | Reaction product of: | Ratio in moles | Water of reaction % | Acid number | Hydroxyl number | Appearance | Soluble in |
| 55 | glycerol/glycolic acid/ behenic acid | 1:3:3 | 97.8 | 38 | 27 | yellowish, very hard, brittle | — |
| 56 | glycerol/glycolic acid/ behenic acid | 1:12:3 | 91.3 | 54 | 71 | brownish-beige, very hard, brittle | — |
| 57 | glycerol/glycolic acid/ palmitic acid | 1:3:3 | 94.4 | 46 | 25 | yellowish, hard, brittle | acetone |
| 58 | glycerol/glycolic acid/ palmitic acid | 1:12:3 | 90.4 | 79 | — | brownish-beige, slightly softer, but still brittle | — |
| 59 | glycerol/glycolic acid/ oleic acid | 1:3:3 | 91.0 | 43 | 35 | dark brown, cloudy, slightly viscous | n-hexane |
| 60 | glycerol/glycolic acid/ oleic acid | 1:12:3 | 89.6 | 62 | 5 | mid-brown, paste-like | — |
| 61 | glycerol/glycolic acid/ linoleic acid | 1:3:3 | 87.5 | 41 | 31 | light brown, clear, slightly viscous | n-hexane |
| 62 | glycerol/glycolic acid/ linoleic acid | 1:12:3 | 87.8 | 67 | — | light brown paste | — |

TABLE 11

| | Reaction products of glycerol, lactic acid, fatty acid | | | | | | |
|---|---|---|---|---|---|---|---|
| Example no. | Reaction product of: | Ratio in moles | Water of reaction % | Acid number | Hydroxyl number | Appearance | Soluble in |
| 63 | glycerol/lactic acid/ behenic acid | 1:3:3 | 95.8 | 38 | 31 | yellowish, hard, extremely brittle | — |
| 64 | glycerol/lactic acid/ behenic acid | 1:12:3 | 100 | 55 | 32 | light brown, hard, brittle | ether |
| 65 | glycerol/lactic acid/ palmitic acid | 1:3:3 | 100 | 42 | 32 | beige, hard, brittle | ether |
| 66 | glycerol/lactic acid/ palmitic acid | 1:12:3 | 100 | 55 | 31 | brownish-yellow, viscous, with extensive crystallization | n-hexane |
| 67 | glycerol/lactic acid/ oleic acid | 1:3:3 | 99.3 | 42 | 34 | light brown, clear, slightly viscous | ethanol |
| 68 | glycerol/lactic acid/ oleic acid | 1:12:3 | 100 | 59 | 27 | mid-brown, clear, viscous | ethanol |
| 69 | glycerol/lactic acid/ linoleic acid | 1:3:3 | 95.9 | 45 | 40 | yellow, clear, slightly viscous | ethanol |
| 70 | glycerol/lactic acid/ linoleic acid | 1:12:3 | 100 | 67 | 50 | light brown, clear viscous | ethanol |

TABLE 12

| | Reaction products of glycerol, glycolic acid, lactic acid, fatty acid | | | | | | |
|---|---|---|---|---|---|---|---|
| Example no. | Reaction product of: | Ratio in moles | Water of reaction % | Acid number | Hydroxyl number | Appearance | Soluble in |
| 71 | glycerol/glycolic acid/ lactic acid/behenic acid | 1:6:6:3 | 96.9 | 58 | 15 | brownish, hard, brittle | — |
| 72 | glycerol/glycolic acid/ lactic acid/palmitic acid | 1:6:6:3 | 100 | 66 | 17 | brownish-yellow, hard | n-hexane |
| 73 | glycerol/glycolic acid/ lactic acid/oleic acid | 1:6:6:3 | 100 | 66 | — | dark brown, clear, highly viscous | ethanol |
| 74 | glycerol/glycolic acid/ lactic acid/linoleic | 1:6:6:3 | 100 | 65 | — | mid-brown, slightly cloudy, viscous | ethanol |

TABLE 12-continued

| | Reaction products of glycerol, glycolic acid, lactic acid, fatty acid | | | | | |
|---|---|---|---|---|---|---|
| Example no. | Reaction product of: acid | Ratio in moles | Water of reaction % | Acid number | Hydroxyl number | Appearance | Soluble in |

5. Reaction Products of Fatty, Acid Mono- and Diglycerides with Lactide

Procedure:

The quantities of lactide and fatty acid glyceride indicated in Tables 13 and 14 are heated with stirring under nitrogen for 1 hour to 195° C. in a standard laboratory apparatus. The components are left to react for 4 hours at 195° C. and the product is decanted without cooling.

An Sn-II-chloride solution in ether was used as catalyst (2.3 ml of a 0.25% solution of SnCl$_2$-ether per mole lactide).

Details of the laboratory mixtures and product properties are shown in Tables 13 and 14.

TABLE 13

| | Reaction products of glycerol monoesters and lactide | | |
|---|---|---|---|
| Example no. | Reaction product of lactide and: | Moles lactide/ OH-equivalent | Appearance and consistency |
| 75 | glycerol monostearate | 0.5:1 | white and solid |
| 76 | glycerol monostearate | 1:1 | white and solid |
| 77 | glycerol monostearate | 2:1 | white and solid |
| 78 | glycerol monooleate | 0.5:1 | mid-brown, clear, slightly viscous |
| 79 | glycerol monooleate | 1:1 | mid-brown, clear, viscous |
| 80 | glycerol monooleate | 2:1 | mid-brown, clear, highly viscous |

TABLE 14

| | Reaction products of glycerol monoesters and lactide | | |
|---|---|---|---|
| Example no. | Reaction product of lactide and: | Moles lactide/ OH-equivalent | Appearance and consistency |
| 81 | glycerol dioleate | 0.5:1 | light brown, clear, thinly viscous |
| 82 | glycerol dioleate | 1:1 | light brown, clear, thinly viscous |
| 83 | glycerol dioleate | 2:1 | light brown, clear, slightly viscous |

TABLE 15

| | Reaction products of glycerol diesters and lactide | | |
|---|---|---|---|
| Example no. | Reaction product of lactide and: | Moles lactide/ OH equivalent | Appearance and consistency |
| 84 | glycerol dioleate | 4:1 | mid-brown, clear, viscous |
| 85 | glycerol dioleate | 8:1 | light brown, very cloudy, solid |
| 86 | glycerol dioleate | 16:1 | light brown, very cloudy, solid |

TABLE 16

| | Reaction products of glycerol monoesters and lactide | | |
|---|---|---|---|
| Example no. | Reaction product of lactide and: | Moles lactide/ OH equivalent | Appearance and consistency |
| 87 | glycerol monooleate | 4:1 | mid-brown, clear, highly viscous |
| 88 | glycerol monooleate | 8:1 | light brown, clear, highly viscous |
| 89 | glycerol monooleate | 16:1 | yellowish, clear, highly viscous to solid |

Table 17 below shows the suitability of oligohydroxycarboxylic acid derivatives (OHCAS) according to the invention for blending with standard commercial disinfectants for a variety of applications, particularly in the field of skin, mucous membrane and/or wound disinfection. Suitable active substances for this purpose are, for example, halogens and halogen-containing preparations, for example iodine preparations, organic heavy metal compounds, quaternary ammonium compounds, guanidine derivatives, aldehydes, oxidizing compounds, acid compounds and the like. Most of the liquid OHCAS selected may be mixed with these antimicrobial agents without the help of solvents. In a few cases, miscibility is only achieved with the assistance of standard solvents, particularly alcohols.

To demonstrate the various possibilities, a choice of disinfecting agents was made for some Examples.

The miscibility of the binary systems (99% by weight OHCA, 1% by weight antimicrobial agent) was determined in a test tube).

Evaluation: + = miscible without sedimentation
− = immiscible

To determine ternary miscibility, OHCA (89% by weight), solvent (10% by weight) and antimicrobial agent (1% by weight) were mixed as described above and evaluated.

Saccharin (proposed as secretion absorber) is soluble in quantities of 5% by weight in all liquid OHCAS apart from the material of Example 62.

TABLE 17

| | Miscibility of liquid OHCAS with antimicrobial agents, if necessary with the aid of solvents | | | | | | |
|---|---|---|---|---|---|---|---|
| | Antimicrobial agents | | | | | | |
| OHCA | Chlorhexidine solution (20%) | Dodigen 1611* (QUAT 50%) | Glyoxal (40%) | $H_2O_2$ (35%) | Irgasan DP 300** (100%, powder) | Lactic acid (90%) | Carbamide (100%, powder) |
| Acc. to Ex. 2 | — | + | + | — | + | + | + |
| Suitable solvents | — | ethanol isopropanol n-propanol propylene glycol dowanol glycerol | ethanol isopropanol n-propanol propylene glycol dowanol glycerol | — | ethanol isopropanol n-propanol propylene glycol dowanol glycerol | ethanol isopropanol n-propanol propylene glycol dowanol glycerol | ethanol isopropanol n-propanol propylene glycol dowanol glycerol |
| Acc. to Ex. 8 | + | + | + | + | + | + | + |
| Suitable solvents | | ethanol, isopropanol, n-propanol, propylene glycol, dowanol, glycerol | | | | | |
| Acc. to Ex. 14 | + | + | + | + | + | + | + |
| Suitable solvents | | ethanol, isopropanol, n-propanol, propylene glycol, dowanol, glycerol | | | | | |
| Acc. to Ex. 69 | — | + | — | — | + | — | + |
| Suitable solvents | — | ethanol isopropanol n-propanol dowanol | n-propanol dowanol | dowanol | ethanol isopropanol n-propanol | — | ethanol isopropanol n-propanol dowanol |

*alkyl-dimethyl-benzylammonium chloride, manufactured by Hoechst, Frankfurt, Germany
**2,4,4'-trichlorodiphenyl ether, manufactured by Ciba-Geigy, Basel, Switzerland Active-component compositions for disinfectants for various applications using the OHCAS according to the invention are shown in Examples 90 to 100 below.

| Hand disinfectant | Example 90 |
|---|---|
| Ethanol (MEK denatured) | 46.0 |
| Isopropanol | 27.0 |
| Benzylalcohol | 1.0 |
| Hydrogen peroxide | 0.1 |
| $C_{8-12}$ fatty acid glyceride | 0.5 |
| Perfume | 0.2 |
| OHCA of Example 8 | 25.0 |
| Water | balance |

| Skin disinfectant | Example 91 | Example 92 |
|---|---|---|
| Isopropanol | 50.0 | 40.0 |
| Chlorhexidine digluconate | 0.5 | 0.5 |
| Hydrogen peroxide | 0.45 | 0.45 |
| $C_{8-12}$ fatty acid glyceride | 0.5 | 0.5 |
| Saccharin | — | 5.0 |
| Perfume | 0.1 | 0.1 |
| OHCA of Example 8 | 25.4 | 30.4 |
| Water | balance | balance |

| Mucous membrane disinfectant | Example 93 | Example 94 |
|---|---|---|
| Ethanol (MEK denatured) | 20.0 | 20.0 |
| Irgasan DP 300 | — | 0.3 |
| Chlorhexidine digluconate | 0.3 | — |
| Hydrogen peroxide | 0.5 | 0.5 |
| Lactic acid | 0.2 | — |
| Castor oil + 40 EO (hydrogenated) | 0.1 | — |
| Propylene glycol | — | 3.0 |
| OHCA of Example 14 | 6.0 | — |
| OHCA of Example 8 | — | 10.0 |
| Water | balance | balance |

| Wound disinfectant, liquid | Example 95 | Example 96 | Example 97 |
|---|---|---|---|
| Ethanol (MEK denatured) | 20.0 | 20.0 | — |
| Chorhexidine digluconate | 0.3 | 0.3 | — |
| Irgasan DP 300 | — | — | 3.0 |
| Hydrogen peroxide | 0.5 | 0.5 | — |
| Lactic acid | 0.2 | 0.2 | 10.0 |
| Castor oil + 40 EO (hydrogenated) | 0.1 | — | — |
| Phenyl salicylate | 0.1 | — | — |
| Glycerol | — | — | 5.0 |
| Vitamin E | — | — | 0.5 |
| Melissa oficinalis | 1.0 | — | — |
| OHCA of Example 14 | 4.0 | — | — |
| OHCA of Example 8 | — | 85.0 | — |
| OHCA of Example 8 | — | — | 20.0 |
| Water | balance | balance | balance |

| Wound disinfectant, powder | Example 98 | Example 99 | Example 100 |
|---|---|---|---|
| Percarbamide | 2.0 | 3.0 | — |
| Lactic acid | 15.0 | — | 15.0 |
| Saccharin | 5.0 | — | — |
| Oxoferine (oxygen-chlorine complex, Oxo-Chemie, Neckarsulm, Germany) | — | 0.2 | — |
| Irgasan DP 300 | — | — | 2.0 |
| OHCA of Example 58 | 78.0 | — | — |
| OHCA of Example 65 | — | 96.8 | — |
| OHCA of Example 54 | — | — | 83.0 |

Permanence Determination

The 16 oligomeric hydroxycarboxylic acid derivatives according to the invention listed in Table 18 below were subjected to an in-vitro test. For this test, the test substances were applied to the excized dorsal skin of hairless rats and the skin thus treated was placed for a total of 24 hours in a SCHAFER/STUTTGEN diffusion chamber, the dermis being bathed in physiological salt solution (chamber water). The temperature in the diffusion chamber was kept at 35° C. In every test, approx. 60 mg of the test substance was applied to a circular area of 1.77 cm² corresponding to the size of the chamber opening. To reduce viscosity, paste-form hydroxycarboxylic acids were heated beforehand to around 60° C. on a water bath. The test substance was applied by microspatula to the skin and the piece of skin thus treated placed in the chamber opening of the glass chamber heated to 35° C. The cutis side of the skin was in contact with the magnetically stirred chamber liquid (physiological salt solution) for the entire duration of the test (24 hours).

The pieces of skin were visually examined every hour for 8 hours by two examiners on the basis of the following criteria regarding the test substances to be applied:
loss of shine/drying out
change of color
change of color intensity spreading beyond the treated surface For re-evaluation, the pieces of skin were left on the chamber opening for 24 hours.

Table 18 below summarizes the tests and visual assessments.

TABLE 18

| Substance Example | Viscosity | Color | Quantity applied (mg/cm$^2$) | Visual assessment |
|---|---|---|---|---|
| 4 | medium | white | 59.5 | no spreading, no loss of shine |
| 5 | medium | white | 28.5 | no spreading, no loss of shine |
| 18 | medium | white | 30.7 | no spreading, no loss of shine |
| 23 | medium | white | 34.7 | no spreading, no loss of shine |
| 25 | paste | white | 27.6 | no spreading, no loss of shine |
| 32 | medium | white | 29.2 | no spreading, no loss of shine |
| 30 | paste | white | 30.3 | shine disappearing after 1–7 h, dull after 24 h |
| 67 | low | yellow | 37.9 | spreading after ca. 3 h |
| 68 | medium | yellow | 32.2 | no spreading, no loss of shine |
| 74 | medium | yellow | 32.3 | slight spreading after ca. 3 h |
| 70 | low | yellow | 40.1 | no spreading, no loss of shine |
| 80 | high | yellow | 40.7 | no spreading, no loss of shine |
| 83 | low | yellow | 28.7 | slight spreading after 2 h |
| 89 | paste | yellow | 29.8 | slight drying out after 6 h |
| 86 | paste | yellow | 38.0 | no spreading, no loss of shine |
| 77 | paste | white | 36.0 | no spreading, no loss of shine |

We claim:

1. A method for dressing wounds to the skin wherein the wound is allowed to breathe, the exudate is absorbed, and the granulation process is accelerated, comprising applying to said wound a vulnery powder comprising as a carrier material a solid powdered oligomeric ester of lactic acid and/or gylcolic acid, or a dermatologically compatible derivative thereof, wherein the oligomeric ester has a degree of oligomerization of up to about 100.

2. The method of claim 1 wherein the wound is open and the vulnery powder forms an artificial scab on the wound in conjunction with fluid from the wound.

3. A method for applying a disinfectant composition to cow udders comprising applying to the cow udders a thinly liquid to paste-like composition containing the disinfectant and as a carrier material an oligomeric ester of lactic acid and/or glycolic acid or a dermatologically compatible derivative thereof to form a non-porous film on the cow udders, and leaving the composition in contact with the cow udders until it is resorbed through the cow udders, and wherein the oligomeric ester or its derivative has an average degree of oligomerization of from 2 to about 50 and the degree of oligomerization is selected to obtain a predetermined time period measured in hours in which the oligomeric ester or its derivative remains in contact with the cow udders before resorption.

4. The method of claim 3 wherein the composition is resorbed through the cow udders in a period of from about 10 to about 12 hours from the time of application.

5. A vulnery powder comprising as carrier material a solid oligomeric ester of lactic acid and/or glycolic acid, or a dermatologically compatible derivative thereof, wherein the oligomeric ester has a degree of oligomerization of up to about 100.

6. The vulnery powder of claim 5 wherein the carrier material is a dermatologically-compatible derivative which is an ester of a monofunctional or polyfunctional alcohol.

7. The vulnery powder of claim 5 wherein the carrier material is a dermatologically-compatible derivative which is an ester of a monofunctional or polyfunctional carboxylic acid.

8. The vulnery powder of claim 5 wherein the carrier material is a dermatologically-compatible derivative which is an ester of a monofunctional or polyfunctional alcohol with the carboxylic acid group of the oligomeric ester and an ester of a monofunctional or polyfunctional carboxylic acid with the hydroxyl group of the oligomeric ester.

9. The vulnery powder of claim 8 wherein the alcohol is a polyfunctional alcohol containing from 2 to 4 hydroxyl groups.

10. The vulnery powder of claim 8 wherein the alcohol is a monofunctional alcohol containing up to 22 carbon atoms.

11. The vulnery powder of claim 10 wherein the monofunctional alcohol contains up to 18 carbon atoms.

12. The vulnery powder of claim 9 wherein the polyfunctional alcohol is glycerol.

13. The vulnery powder of claim 12 wherein the derivative is also a derivative of a monocarboxylic acid.

14. The vulnery powder of claim 5 wherein the carrier material is a dermatologically-compatible derivative wherein the derivative is a derivative of a fatty acid mono-, di- or triglyceride.

15. The vulnery powder of claim 5 wherein the carrier material is a dermatologically-compatible derivative which is a derivative of a natural or synthetic fat, wax or oil.

16. The vulnery powder of claim 5 wherein the oligomeric ester contains free carboxyl groups.

17. The vulnery powder of claim 5 in which the average degree of oligomerization of the oligomeric ester or its derivative is from 2 to 25.

18. The vulnery powder of claim 5 wherein the vulnery powder also contains pharmacologically active material for treatment of the wound.

19. The method of claim 3 wherein a dermatologically-compatible derivative is employed which is an ester of a monofunctional or polyfunctional alcohol or carboxylic acid.

* * * * *